(12) United States Patent
Winterwerber (10) Patent No.: US 12,420,081 B2
(45) Date of Patent: Sep. 23, 2025

(54) BLOOD PUMP FOR SUPPORTING HEART FUNCTION AND METHOD FOR PRODUCING A PUMP HOUSING OF A BLOOD PUMP

(71) Applicant: Berlin Heart GmbH, Berlin (DE)

(72) Inventor: Kim Winterwerber, Erlangen (DE)

(73) Assignee: Berlin Heart GmbH, Berlin (DE)

( * ) Notice: Subject to any disclaimer, the term of this patent is extended or adjusted under 35 U.S.C. 154(b) by 1155 days.

(21) Appl. No.: 17/296,433

(22) PCT Filed: Nov. 25, 2019

(86) PCT No.: PCT/EP2019/082390
§ 371 (c)(1),
(2) Date: May 24, 2021

(87) PCT Pub. No.: WO2020/109216
PCT Pub. Date: Jun. 4, 2020

(65) Prior Publication Data
US 2022/0016411 A1    Jan. 20, 2022

(30) Foreign Application Priority Data
Nov. 26, 2018    (EP) ..................................... 18208218

(51) Int. Cl.
*A61M 60/816*    (2021.01)
*A61M 60/148*    (2021.01)
(Continued)

(52) U.S. Cl.
CPC ........ *A61M 60/816* (2021.01); *A61M 60/148* (2021.01); *A61M 60/178* (2021.01);
(Continued)

(58) Field of Classification Search
CPC .............. A61M 60/122; A61M 60/148; A61M 60/816; A61M 2205/3306; A61M 60/216;
(Continued)

(56) References Cited

U.S. PATENT DOCUMENTS 5,594,819 A * 1/1997 Narendran ............. G01B 11/18
385/12
2015/0080743 A1* 3/2015 Siess .................... A61B 5/0036
600/478

(Continued)

FOREIGN PATENT DOCUMENTS

DE    10 2009 014 462 A1    1/2011
EP    3 090 767 A1    11/2016
(Continued)

OTHER PUBLICATIONS

International Search Report for Application No. PCT/EP2019/082390, dated Feb. 24, 2020, European Patent Office, Rijswijk, Netherlands, pp. 1-6.
(Continued)

*Primary Examiner* — Sarah W Aleman
(74) *Attorney, Agent, or Firm* — Crowell & Moring LLP (57) ABSTRACT

A blood pump may be provided for supporting heart function. A method may be provided for producing a pump housing of the blood pump. The provided blood pump comprises an implantable pump housing. The blood pump additionally comprises a fiber optic sensor comprising an optical fiber. The optical fiber is at least partially accommodated in a housing part of the pump housing.

21 Claims, 6 Drawing Sheets

(51) Int. Cl.
*A61M 60/178* (2021.01)
*A61M 60/216* (2021.01)
*A61M 60/531* (2021.01)
*A61M 60/554* (2021.01)

(52) U.S. Cl.
CPC ........ *A61M 60/216* (2021.01); *A61M 60/531* (2021.01); *A61M 60/554* (2021.01)

(58) Field of Classification Search
CPC .............. A61M 60/531; A61M 60/554; A61B 5/02154; A61B 5/0261
See application file for complete search history.

(56) References Cited

U.S. PATENT DOCUMENTS

| 2017/0348470 A1* | 12/2017 | D'Ambrosio | ....... A61M 60/816 |
| 2018/0311422 A1* | 11/2018 | Greatrex | ............ A61M 60/183 |

FOREIGN PATENT DOCUMENTS

| EP | 3 108 809 A1 | 12/2016 |
| WO | WO 2013/160443 A1 | 10/2013 |
| WO | WO 2015/160943 A1 | 10/2015 |
| WO | WO 2017/205909 A1 | 12/2017 |
| WO | WO 2017/214118 A1 | 12/2017 |

OTHER PUBLICATIONS

Office Action dated Apr. 20, 2024 for China Patent Application No. 2019800772258 (Chinese language), with English translation identifying references WO 2017/205909 A1 and WO 2017/214118 A1 (previously disclosed in the file as IDS references A4 and A5, respectively).

* cited by examiner

BLOOD PUMP FOR SUPPORTING HEART FUNCTION AND METHOD FOR PRODUCING A PUMP HOUSING OF A BLOOD PUMP

CROSS-REFERENCE TO RELATED APPLICATIONS

This application is a 371 nationalization of international patent application PCT/EP2019/082390 filed Nov. 25, 2019, which claims priority under 35 USC § 119 to European patent application 18208218.0 filed Nov. 26, 2018. The entire contents of each of the above-identified applications are hereby incorporated by reference.

DETAILED DESCRIPTION

The present application resides in the field of medical technology and in particular in the field of implantable blood pumps for supporting heart function. The application relates to a blood pump for supporting heart function. The present application further relates to a method for producing a pump housing.

Blood pumps are known from the state of the art. These blood pumps can be used when a patient's heart function requires support or replacement. Common systems used are so-called ventricular assist devices (VAD). Such heart pumps can be implemented, for example, as so-called left ventricular assist devices (LVAD), right ventricular assist devices (RVAD) or bi-ventricular assist devices (BiVAD). In addition to the blood pump, which during operation is implanted in the patient, these systems in general comprise a control unit, which is arranged outside a patient's body and connected to the blood pump via a percutaneous line (driveline). The blood pump in general comprises a motor including a stator and a rotor provided with blades. The motor of the blood pump can be driven by electric power supplied by the control unit, for example in that a current flow is generated in windings of the stator, which causes the rotor, including the blades, to rotate so as to deliver blood of the patient. In some embodiments, known systems for supporting heart function can comprise a blood pressure sensor. In addition, a regulating device for regulating the blood pump can be provided, which sets a conveying performance of the heart pump based on blood pressure values that were ascertained by the blood pressure sensor. Systems of the related type are described in the published prior art EP 3 090 767 A1 and EP 3 108 809 A1, for example.

It is an object of the present application to provide an improved blood pump. In particular, it is an object of the present application to provide a blood pump that is particularly durable and has a compact design. It is also an object of the present application to provide an accordingly advantageous method for producing a pump housing.

Advantageous refinements will be apparent from the features of the dependent claims and the exemplary embodiments.

The provided blood pump is suitable for supporting heart function. The blood pump comprises an implantable pump housing. The blood pump additionally comprises a fiber optic sensors including an optical fiber. The optical fiber is at least partially accommodated in a housing part of the pump housing.

As a result of the optical fiber being accommodated in the housing part of the pump housing of the blood pump, a particularly robust and compact design of the blood pump equipped with a sensor can be achieved. In typical embodiments, the fiber optic sensor also comprises a light source, a light detector and/or an evaluation unit or is connected or connectable thereto. The optical fiber can be used to transmit an optical variable, which represents a measured variable to be detected by the sensor, between an actual measurement site and the evaluation unit. The light source is generally configured to couple light into the optical fiber. In some embodiments, the light source can be accommodated in the pump housing and/or be rigidly connected thereto. The light detector is generally configured to detect light exiting the optical fiber. In some embodiments, the light detector can be accommodated in the pump housing and/or be rigidly connected thereto. The evaluation unit can, for example, likewise be accommodated in the pump housing and/or be rigidly connected thereto. The evaluation unit is typically connected to the light detector and can be configured for data processing and, for this purpose, can comprise a processor and a data memory, for example. The measurement site is generally located in the periphery of the pump housing, for example on an outer side of the pump housing or on an inner side of the pump housing. As a result of the provided blood pump comprises a fiber optical sensor including an optical fiber, the measurement site of the sensor can be established in a particularly compact manner, without necessitating considerable modifications of the blood pump to provide the sensor.

One problem that can occur with known sensor types of blood pumps and is avoided by the provided blood pump, is insufficient sealing between a pick-up or a transmission channel and an evaluation unit connected to the pick-up via the transmission channel. For example, with the known sensor types, the transmission channel can be used to electrically or pneumatically transmit a variable, which represents a measured variable detected by the sensor, between an actual measurement site and the evaluation unit. When the evaluation unit is accommodated in a pump housing, for example, the sealing between the transmission channel or the pick-up and a housing part of the pump housing accommodating the pick-up or the transmission channel may, for example, be achieved only insufficiently by a plastic seal, since blood coming in contact with the plastic seal, in the case of an implanted blood pump, may constitute an aggressive medium for common types of plastic seals, which, on the one hand, can degrade the material of the plastic seal and, on the other hand, is able to diffuse through this material, resulting in impairment of the long-term stability of known blood pumps.

Due to the provision of an optical fiber, which is accommodated in the housing part of the pump housing, the use of conventional plastic seals can be dispensed with, so that the provided blood pump has particular long-term stability.

The application also relates to a corresponding advantageous method for producing a pump housing of a blood pump. An optical fiber is provided in the provided method. In addition, a first metal piece is provided. The optical fiber is arranged on the first metal piece. Thereafter, the optical fiber is at least partially covered with a second metal piece. The optical fiber can furthermore be embedded into the metal pieces. For this purpose, ultrasonic energy can be introduced into the first and/or second metal piece, wherein, however, it is also possible, for example, to introduce thermal energy. In this way, the first and the second metal piece can be joined. The metal pieces can be made of the same material.

Furthermore, the optical fiber can be enclosed in the metal pieces in such a way that the optical fiber is at least partially embedded circumferentially, in particular without gaps, into a housing part that is formed of the first metal piece and the second metal piece. In some embodiments, the optical fiber is material-bonded to the metal pieces or the housing part. In this case, regions of the metal pieces can form a ring extending around the optical fiber. For example, a region of the housing part can form a closed ring extending around the optical fiber. In this way, the housing part and the optical fiber form a particularly reliable seal. The region of the housing part surrounding the optical fiber is advantageously designed in one piece, so that particularly reliable sealing is achieved.

The optical fiber typically comprises a light-guiding core. In some embodiments, the light-guiding core can comprise plastic fibers, for example acrylic resin fibers. However, it is advantageous, especially with respect to the above-described sealing properties and the long-term stability of the blood pump, when the light-guiding core contains glass fibers, so that a diffusion of blood into the light-guiding core is avoided or reduced.

In some embodiments, the light-guiding core of the optical fiber is cladded. For example, the light-guiding core can be coated. Typically, a cladding made of a metal is suitable, so as to circumvent the above-described problems of plastic-based materials. Moreover, particularly good sealing can thus be achieved between the optical fiber and the housing part. For example, the cladding can comprise the same material as the housing part of the pump housing or consist thereof. In general, materials of at least those portions of the housing part, or of the cladding, which come in contact with blood during use of the blood pump in the body of a patient are biocompatible. The cladding of the optical fiber and/or the housing part, in particular the metal pieces, can advantageously contain titanium, and in particular a titanium alloy. For example, the housing part, in particular the metal pieces, or the optical fiber can be produced from titanium or from the titanium alloy. In this way, the housing part or the cladding is biocompatible and particularly corrosion-resistant.

In general, an end face of a fiber end of the optical fiber which is accommodated in the housing part of the pump housing is not completely covered by the housing part. A pick-up of the fiber optic sensor connected to the fiber end, or formed by the fiber end, is generally not completely covered by the housing part, so that the sensor is configured to make contact with an interior of the patient's body, and in particular with blood of the patient. The provided blood pump can be particularly corrosion-resistant in that the fiber end is embedded into the housing part in such a way that the fiber end and the housing part form a plastic-free seal. In this way, it is avoided that blood penetrates into portions of the seal, which may occur, for example, in the case of sealing with polymer parts.

The blood pump generally comprises a motor. The motor typically comprises a stator, for example comprising windings, and a rotor, for example comprising a permanent magnet. The motor is typically at least partially, and in particular completely, accommodated in the pump housing. In addition, the pump housing surrounds and/or defines a flow channel for conveying blood. The rotor, which can be designed as a conveying element or connected to a conveying element, is typically arranged in the flow channel. The conveying element is generally likewise arranged in the flow channel. The pump housing generally includes an inlet arranged upstream of the conveying element, and an outlet arranged downstream of the conveying element. The inlet can comprise an inlet cannula. The pump housing can furthermore comprise a chamber half. A region of the chamber half can form the outlet of the pump housing. A portion of the flow channel delimited by the chamber half can be substantially spiral-shaped.

In general, the measurement value measured by the fiber optical sensor is detected in the region of an end face of the optical fiber. In some embodiments, it can be provided that the optical fiber, with the end face thereof, faces the flow channel and/or opens into the flow channel for delivering blood. In particular, it may be provided that the optical fiber is arranged so that the measurement site is located in the flow channel. In some embodiments, it can furthermore be provided that the end face of the optical fiber is separated from the flow channel by the pick-up of the sensor. However, it can also be provided that the end face of the optical fiber is configured to be in direct contact with the flow channel. For example, the light-guiding core of the optical fiber can be configured and arranged to make contact with blood of the patient. The flow channel can be at least partially delimited by an interior side of the housing part. The blood pump can be particularly advantageous when the optical fiber, with the end face thereof, faces the flow channel since the sensor, due to a comparatively small dimension of the optical fiber compared to other sensor types, requires only a modification of the delimitation of the flow channel that is limited to a small area. In general, the need to modify the delimitation of the flow channel can be the result of a difference in the shape or the material of a wall of the flow channel caused by the sensor. In this way, due to the use of the optical fiber which, in particular compared to conventional translucent windows, can have a small cross-section, the blood pump can be configured to be particularly gentle on the blood. A cross-section of the optical fiber can, for example, be no more than 1 mm, preferably no more than 500 µm, and particularly preferably no more than 200 µm.

In some embodiments, it may be provided that the end face of the optical fiber is arranged at a section of the flow channel located upstream with respect to the conveying element. For example, the optical fiber can open into the flow channel at the upstream section, or the pick-up can be arranged in this section. In this case, a measurement of blood parameters, using the fiber optic sensor, is particularly reliable since the blood, at the inlet, has not yet made contact with the conveying element and is not yet influenced or damaged thereby. The housing part in which the optical fiber is accommodated can, for example, be formed by the inlet cannula of the pump housing. In other embodiments, the optical fiber opens into the flow channel at a downstream section, or the pick-up is arranged in this section. In this case, the housing part in which the optical fiber is accommodated can, for example, be formed by the chamber half of the pump housing.

In some embodiments, the blood pump can comprise a regulating device. The regulating device can be connected to the evaluation unit. The regulating device is typically configured for data processing and, for this purpose, comprises a processor and a data memory, for example. The regulating device can be connected to the fiber optic sensor and the motor of the blood pump. The regulating device can furthermore be configured to set a conveying performance of the blood pump based on measurement values that were ascertained by the fiber optic sensor. For example, in a method for supporting the heart initially a blood pump, as described above or below, can be provided and implanted. Moreover, a conveying performance of the blood pump can be set based on the measurement values that were ascertained by the fiber optic sensor.

In some embodiments, it is provided that the fiber optic sensor is a sensor for determining blood parameters. For example, the sensor can be a blood pressure sensor. For example, the blood pressure sensor can comprise a Fabry-Perot cavity or a fiber Bragg grating. In particular when the fiber optic sensor is a blood pressure sensor, the evaluation unit can be configured to determine a flow of the delivered blood based on the blood pressure values measured by the fiber optic sensor. The regulating device can be configured to activate the motor of the blood pump based on the determined values of the flow, for example in that the regulating device adapts the flow to a desired target flow.

In some embodiments, the fiber optic sensor can be configured to determine further blood parameters, aside from the blood pressure or in addition to the blood pressure, such as a hematocrit value, a blood sugar level and/or a blood oxygen level. Moreover, it may be provided that the fiber optic sensor is a sensor for thrombi detection.

In some embodiments, the fiber optic sensor is configured to detect a position of the conveying element. For this purpose, the fiber end of the optical fiber can be arranged in the region of the conveying element. The end face of the optical fiber can, for example, be directed at the conveying element. The evaluation unit can be configured, for example, to determine the position of the conveying element based on detected light scattered back by the conveying element. In this way, for example, a wobble movement of the conveying element during operation of the blood pump can be detected, based on which the evaluation unit can determine a viscosity of the blood. The regulating device can, in turn, be configured to activate the motor of the blood pump based on the determined viscosity of the blood.

It may be provided that the optical fiber, with the end face thereof, faces an outer side of the pump housing delimited by an exterior side of the housing part. It may be provided, for example, that the optical fiber, with the end face thereof, opens into an outer side of the pump housing delimited by an exterior side of the housing part. In particular, it may be provided that the optical fiber is arranged so that the measurement site is located on the outer side of the pump housing.

When the end face of the optical fiber is to face an interior housing part, for example the flow channel, or an exterior housing part, a subtractive manufacturing step may be provided during the production method for the pump housing for forming the end face of the optical fiber. For example, material can be removed, in particular ground, from the metal pieces and/or the optical fiber, for example after the optical fiber has been embedded into the metal pieces, so that the end face of the optical fiber ends flush with the metal pieces. In this way, it can be achieved that the optical fiber, together with the housing part, forms a shared, smooth surface so that blood flowing past during use of the blood pump is not damaged or only to a minor degree. The fiber optic sensor can thus comprise a common ground surface, which in regions comprises a ground end face of the optical fiber and a ground surface of the pump housing, which is aligned with the end face and extends circumferentially around the same. The shared ground surface can form part of the delimitation of the flow channel, for example.

In some embodiments, it may additionally be provided that the fiber optic sensor comprises a second optical fiber. The optical fibers can be arranged and configured in such a way that the fiber optic sensor is a fiber optic transmission sensor. Both optical fibers can open into the flow channel, for example. End faces of the optical fibers typically face one another in such a way that light, which is coupled into the first optical fiber, is coupled into the end face of the second optical fiber after passing through the flow channel. After having passed through the second optical fiber, the light can be detected by way of a light detector and evaluated by the evaluation unit. In this way, blood parameters can be inferred, such as a hematocrit value or a thrombi density or a presence of thrombi.

In some embodiments, the blood pump can comprise at least two fiber optic sensors, which can be designed as described above or below. For example, the blood pump can comprise a second fiber optic sensor. It may be provided that the first fiber optic sensor is configured to measure a blood pressure in the flow channel delimited by the interior side of the housing part conveying blood. The second fiber optic sensor can be configured to measure a blood pressure either in the flow channel or at an outer side of the pump housing.

To the extent that the second fiber optic sensor is configured to measure the blood pressure in the flow channel, it is particularly advantageous when one of the sensor is arranged upstream with respect to the conveying element, and the second of the sensors is arranged downstream with respect to the conveying element. In this way, the evaluation unit is able to determine the flow of the delivered blood in a particularly simple manner from the two measured blood pressure values.

When the second fiber optic sensor, or a further fiber optic sensor, which can be designed the same as the first fiber optic sensor and/or the second fiber optic sensor, is configured to determine the blood pressure on an outer side of the pump housing, the blood pressure can be determined particularly precisely in that the evaluation unit is configured to determine disturbances on the blood pressure measurement based on the blood pressure values measured on the outer side of the pump housing, and to correct the blood pressure values determined in the flow channel based on the disturbances.

A particular advantage of the provided pump is that the optical fiber is embedded into the housing part and that, as a result, the diffusion of blood both into the optical fiber and into the interface between the housing part and the optical fiber can be avoided. In this way, the durability of the blood pump can be increased, and the functional capability of the blood pump can be ensured. For this purpose, it may be provided that the optical fiber is embedded into the housing part in such a way than the optical fiber and the housing part form a plastic-free seal. The optical fiber can furthermore be welded into the housing part. In particular, it may be provided that the optical fiber is welded into the housing part by way of ultrasonic welding. In this way, particularly effective sealing can be ensured. In addition or as an alternative, the optical fiber can comprise a plastic-free light-guiding core. In particular, the light-guiding core can comprise glass and/or be produced from glass. It may also be provided that a plastic-free component of the optical fiber, and in particular the light-guiding core of the optical fiber, makes direct contact with the housing part. The optical fiber can be material-bonded to the housing part.

Features described above or below with respect to the blood pump for supporting heart function can be applied to the method for producing the pump housing, and vice versa.

Exemplary embodiments will be described hereafter based on the figures.

Figure 1:
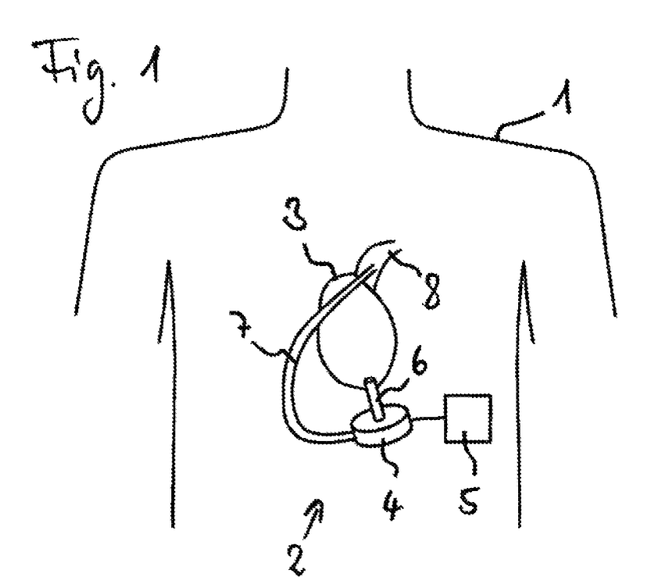
FIG. 1 shows a schematic view of a blood pump, which is implanted in the body of a patient.

FIG. 1 schematically shows a body 1 of a patient in which a blood pump 2 for supporting a function of the heart 3 is implanted. The blood pump 2 comprises a motor that is typically implemented as an electric motor, including a rotatable conveying element, and accommodated in a pump housing 4 of the blood pump 2. The pump housing 4 is connected to a control unit 5, which can likewise be implanted, as is schematically shown. In some embodiments, the control unit 5 can likewise be completely or partially accommodated in the implanted pump housing 4. In other embodiments, the control unit 5 is arranged extracorporeally. The pump housing 4 additionally comprises an inlet port 6, which is connected to an inlet cannula of the pump housing 4 and via which blood can be withdrawn from a ventricle of the heart 3 and delivered via a cannula 7 into a blood vessel 8. The control unit 5 is configured to activate the motor of the blood pump 2 for conveying blood.

Figure 2:
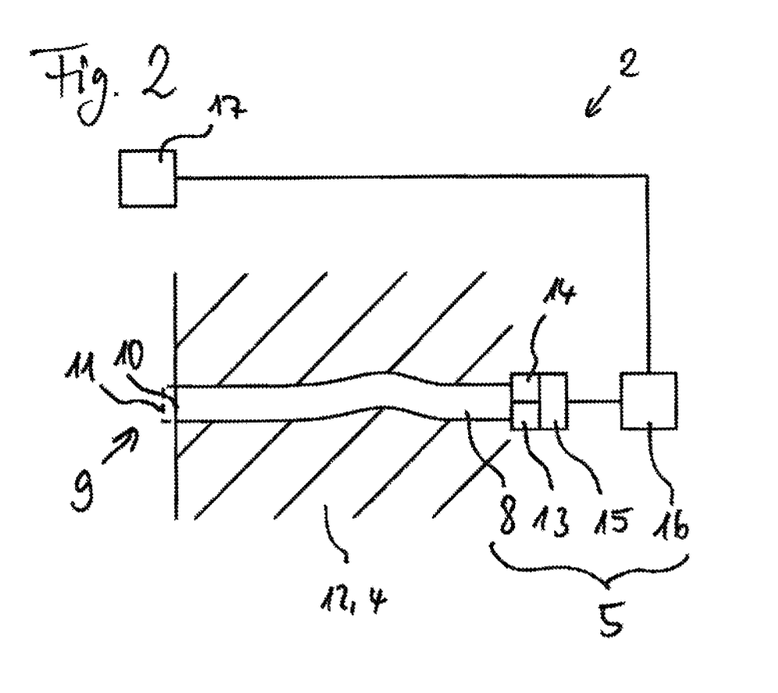
FIG. 2 shows a schematic view of a fiber optic sensor of the blood pump.

FIG. 2 shows a schematic illustration of the blood pump 2. Recurring features are denoted by like reference numerals in this figure and the subsequent figures. The blood pump 2 comprises a fiber optic sensor including an optical fiber 8. The fiber optic sensor is configured to measure measurement values, such as a blood pressure, a hematocrit value, a thrombi density, a blood sugar level, a blood oxygen level or a rotor position, at a measurement site 9. The measurement site 9 is determined by the position of an end face 10 of the optical fiber 8 or a pick-up 11, which is optionally arranged on this end face 10. The optical fiber 8, or at least a portion of the optical fiber 8, is embedded into a housing part 12, for example a titanium part, of the pump housing 4, so that the housing part 12 completely surrounded the optical fiber 8 at least in a region, and so that the optical fiber 8 and the housing part 12 are blood-tight, and at the same time plastic-free. An end of the optical fiber 8 facing away from the end face 10 opens into a light source 13, for example a light-emitting diode, and a light detector 14. The light source 13 is configured to emit light and to couple it into the optical fiber 8, while the light detector 14 is configured to detect light exiting the optical fiber 8. The light source 13 and the light detector 14 are connected to an electronic evaluation unit 15, which is configured to activate the light source 13 and to read out the light detector 14. The evaluation unit 15 is configured to determine the aforementioned measurement values based on the light detected by the light detector 14. The evaluation unit 15 is furthermore connected to an electronic regulating device 16. Based on the measurement values transmitted by the evaluation unit 15 to the regulating device 16, the regulating device 16 is able to activate the motor 17 of the blood pump 2 connected to it, for example in that the regulating device 16 adapts a current flow in windings of the stator.

Figure 3A:
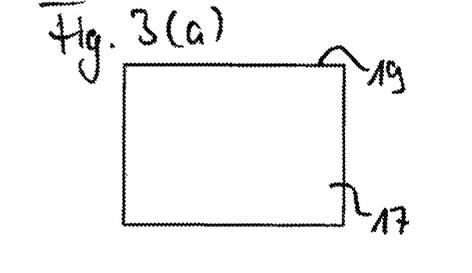
FIGS. 3(a) to (g) show schematic illustrations of method steps during the production of the blood pump.
Figure 3B:
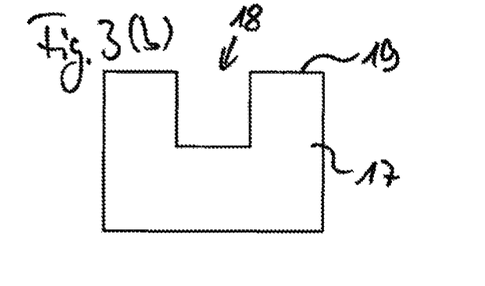
Figure 3C:
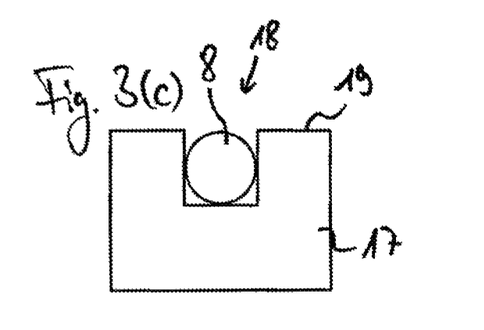
Figure 3D:
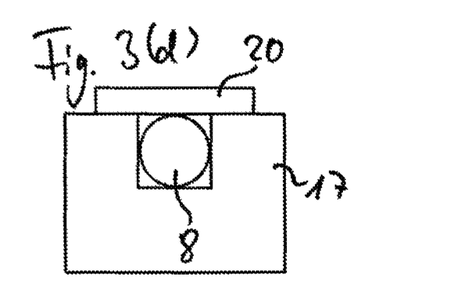

FIGS. 3(a) through (g) schematically illustrate different method steps during a production of the blood pump 2 and the pump housing 4. Initially a first metal piece 17, for example a biocompatible titanium or titanium alloy piece, is provided, which, after production, is to form a piece of the housing part 12 of the pump housing 4, for example a chamber half or an inlet cannula. Afterwards, a recess 18, for example a groove, is generated on a surface 19 of the metal piece 17. The recess 18 can be milled, for example. In a further step, the optical fiber 8 is inserted into the recess 18 and covered by a second metal piece 20, which is made of the same material as the first metal piece 17, as is shown in FIG. 3(d).

Figure 3E:
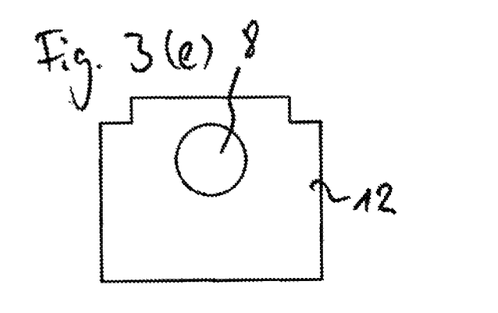

Thereafter, the optical fiber 8 is embedded into the metal pieces 17, 20, so that the metal pieces 17, 20 continuously surround the optical fiber 8, as is shown in FIG. 3(e). In particular, the optical fiber, after production, is at least partially embedded into the housing part such as to extend circumferentially. For this purpose, an ultrasonic sonotrode can be used, which introduces ultrasonic energy into the first and second metal pieces 17, 20. The metal pieces 17, 20 are additionally joined to one another as a result of the introduction of the ultrasonic energy, so that they form a single-piece housing part 12. In some embodiments, the optical fiber 8 can comprise a light-guiding core made of glass fibers or glass fiber bundles, and additionally a metal coating, in particular made of titanium or a titanium alloy, so that a material bond is generated between the coating of the optical fiber 8 and the metal pieces 17, 10 during the embedding of the optical fiber 8.

Figure 3F:
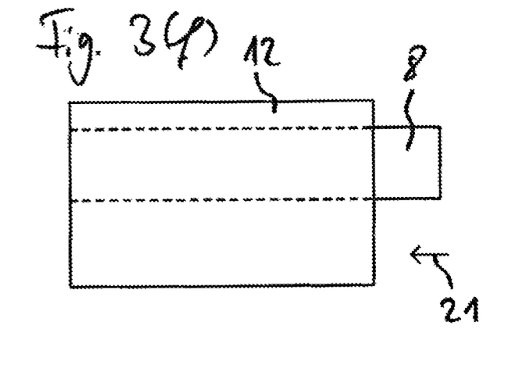
Figure 3G:
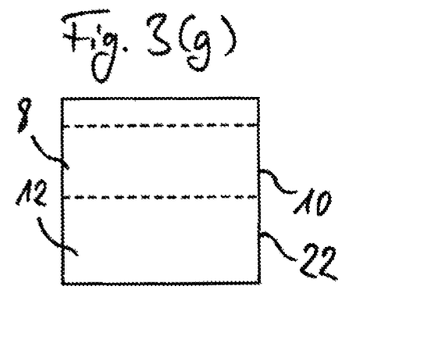

FIGS. 3(f) and (g) show side views of an arrangement after the embedding. A portion of the optical fiber 8 is completely embedded into the housing part 12 formed of the metal pieces 17, 20, this portion only being shown by way of dotted lines in the figure. FIG. 3(f) corresponds to the arrangement shown in FIG. 3(e). In a further step, the arrangement is ground from one side in the direction of the arrow denoted by reference numeral 21. After grinding, the optical fiber 8 and the housing part 17 form a shared ground surface 22, which can form an outer wall of the completed pump housing 4 or a delimitation of a blood-conducting flow channel in the interior of the pump housing 4.

Figure 4A:
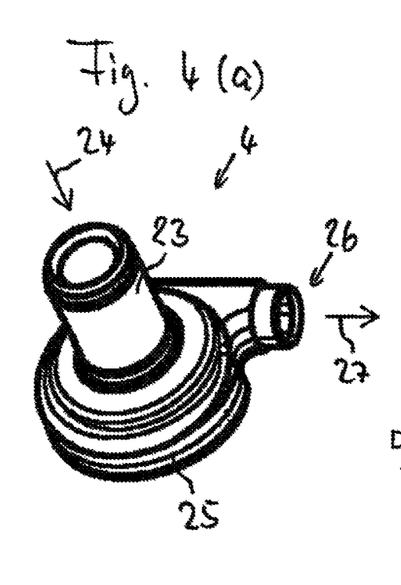
FIGS. 4(a) to (d) show schematic views of a pump housing of the blood pump.

FIGS. 4(a) to (d) show different views of the pump housing 4 of the blood pump 2. FIG. 4(a) shows a perspective outside view of the pump housing 4. The pump housing 4 comprises an inlet cannula 23, into which, during operation of the blood pump 2, blood from heart 3 flows in the direction of the arrow denoted by reference numeral 24. In addition, the pump housing 4 comprises the chamber half 25, which forms a lower partial delimitation of an outlet opening 26, from which, during operation of the blood pump 2, blood flows in the direction of the arrow denoted by reference numeral 27 into the cannula 7 and the blood vessel 8.

Figure 4B:
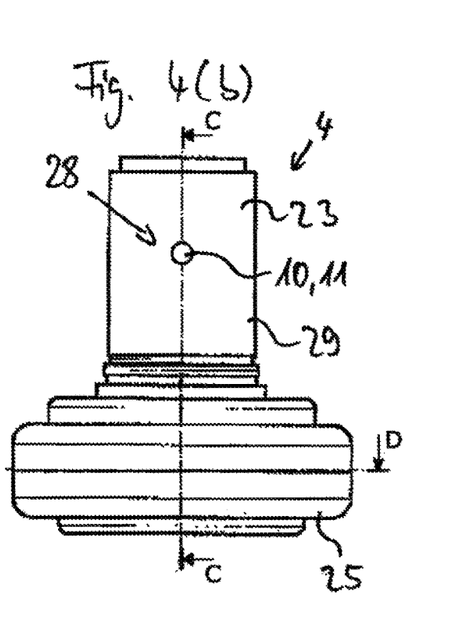

FIG. 4(b) shows a side view of the pump housing 4. A fiber optic sensor 28 is also shown in this illustration, which is designed as described above and the measurement site of which is arranged on an outer side 29 of the inlet cannula 23 of the pump housing 4. The end face 10 of the optical fiber 8, or the possibly provided pick-up 11 of the fiber optic sensor 28 covering the end face 10, is implemented flush with the outer side 29 of the inlet cannula 23.

Figures 4C, 4D:
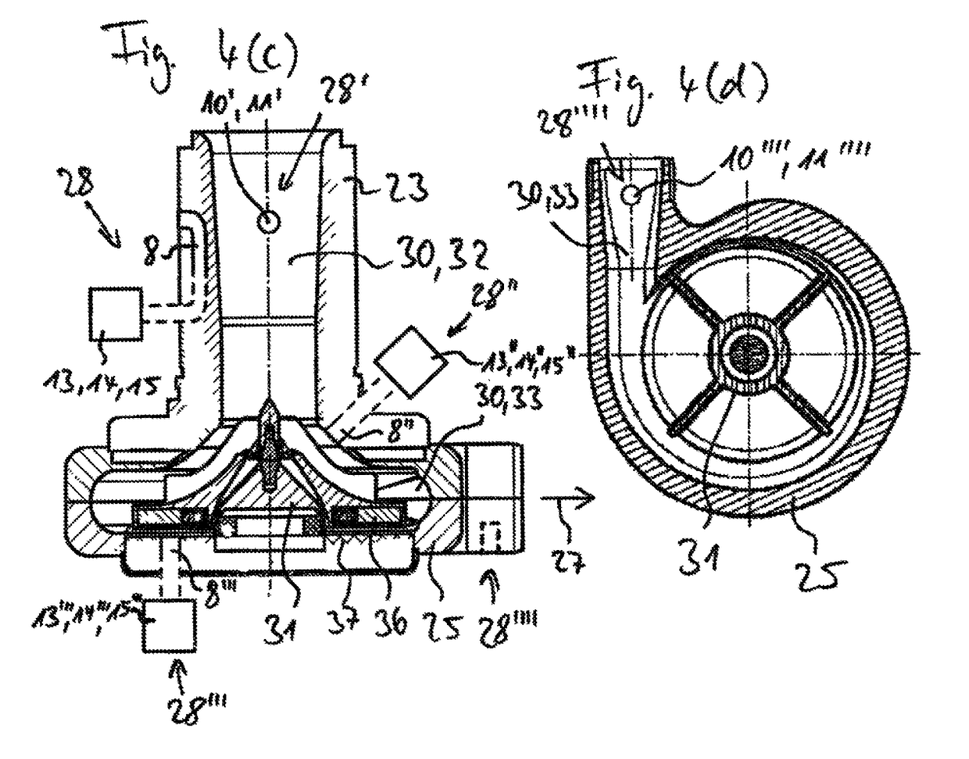

FIGS. 4(c) and (d) each show a cross-sectional view through the pump housing 4 along an intersecting line denoted in FIG. 4(b) by letter C or D. Interior walls of the pump housing 4 forms a flow channel 30, in which a rotor 31 is accommodated. A rotor 31 is provided in the shown example, which is designed as a radial rotor. The rotor 31 is configured in this case to accelerate blood flowing axially in direction 24 via the inlet cannula 23 in the radial direction, and to conduct it in direction 27 into the cannula 7. In other embodiments, however, the blood pump 2 described here can also be designed accordingly as an axial pump comprising an axially delivering rotor. The rotor 31 divides the flow channel 30 into a section 32 located upstream and a section 33 located downstream. The rotor 31 comprises a rotor magnet 36, which is configured to cooperate with stator windings 37 accommodated in the chamber half 25 for driving the motor 17.

According to the above-described method, the optical fiber 8 of the fiber optic sensor 28 is embedded into the inlet cannula 23 of the pump housing 4. In addition, the light source 13, the light detector 14, and the evaluation unit 15 are schematically illustrated, which are connected to the optical fiber 8 and, for example, can be arranged outside the pump housing 4, and in particular outside the body 1 of the patient, or, in some embodiments, can be integrated into the pump housing 4.

In addition to the described fiber optic sensor 28, the blood pump 2 comprises further fiber optic sensors 28', 28", 28''', 28'''', which can be designed corresponding to the described fiber optic sensor 28. An end face 10' of the optical fiber, or a pick-up 11' of the sensor covering the end face 10' denoted by reference numeral 28', is arranged and oriented in such a way that the measurement site of this sensor 28' is located in the section 32 of the flow channel 30 located upstream.

The sensors bearing reference numerals 28" and 28''' are directed at the rotor 31 and can be configured to determine a position of the rotor 31. However, similarly to all other sensors described above or below, these sensors 28", 28" can also be designed as measuring sensors for a blood pressure, a hematocrit value, a thrombi density, a blood sugar level, or a blood oxygen level. In this case, the optical fiber 8" of one of the sensors 28" is embedded into the inlet cannula 23, while the optical fiber 8" of the other sensor 28" is embedded into the chamber half 25.

In FIG. 4(c), the position of a further fiber optic sensor 28'''', which can be designed similarly to the other above-described sensors, is denoted by a dotted line, wherein an exact measurement site can be identified in FIG. 4(d) based on the end face 10'''' or a pick-up 11'''', which covers the end face 10'''' and may be present, in the section 33 of the flow channel 30 located downstream.

The evaluation units of the sensors 28, 28', 28", 28''', 28'''' can, for example, be separate components, as is shown in FIG. 4(c) based on the evaluation units 15, 15" and 15''' shown by way of example. However, it is also possible for some or all of the evaluation units to be combined in a single electronic unit. The evaluation unit or the evaluation units can, as described above, be connected to the regulating device 16. In particular when the sensors denoted by reference numerals 28, 28' and 28''' are implemented as blood pressure sensors, the regulating device 16 can be configured to activate the motor 17 of the blood pump 2 based on differences, for example, in the blood pressure values detected by the sensors denoted by reference numerals 28' and 28'''' and/or differences in the blood pressure values detected by the sensors denoted by reference numerals 28 and 28' or 28 and 28''''.

Figure 5:
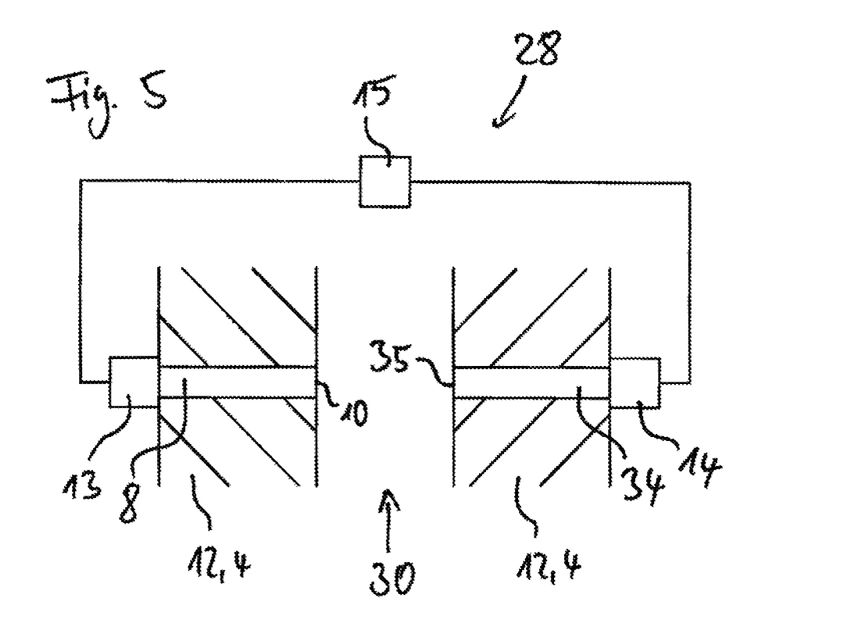
FIG. 5 shows a schematic view of a further fiber optic sensor of the blood pump.

FIG. 5 shows a further embodiment of a fiber optic sensor 28, which is designed as a transmission sensor. This sensor comprises a further optical fiber 34, in addition to the optical fiber 8. In the shown example, the optical fibers 8, 34 are each embedded into the housing part 12 of the pump housing 4, as described above, wherein the housing part 12 partially surrounds a blood-conducting region, for example the flow channel 30.

The light source 13 is arranged in such a way that light emitted thereby can be coupled into the optical fiber 8. The optical fibers 8, 34 are arranged and oriented, with the end faces 10, 35, in such a way that light exiting the end face 10 of the one optical fiber 8 passes through the flow channel 30, and enters the second optical fiber 34 via the end face 35 thereof. The light can subsequently be detected by way of the light detector 14 connected to another end of the second optical fiber 34. As described above, the evaluation unit 15 is connected to the light detector 14 and to the light source 13.

Figure 6A:
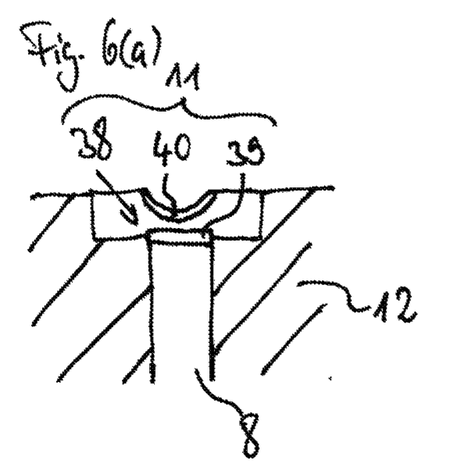
FIGS. 6(a) and (b) show schematic views of fiber optic sensors of the blood pump designed as blood pressure sensors.

FIG. 6(a) schematically shows a fiber optic sensor of the blood pump 2 for blood pressure measurement, which comprises a Fabry-Perot cavity 38. During the blood pressure measurement using this sensor, the flow cell or the pick-up 11 comprises two partially reflective mirrors 39, 40, which can be characterized by high reflectivity and together form an optical resonator. A mirror 40 adjoining the measurement site 9 of the sensor is designed to be flexible, for example in the form of a diaphragm. The spectrum of the arrangement shows narrow intensity maxima for wavelengths that meet the resonance requirements, while other spectral regions are almost completely extinguished. Light spectrum impinging on the pick-up 11 through the optical fiber 8 and reflected thereby can be used by the evaluation unit 15 to infer the blood pressure.

Figure 6B:
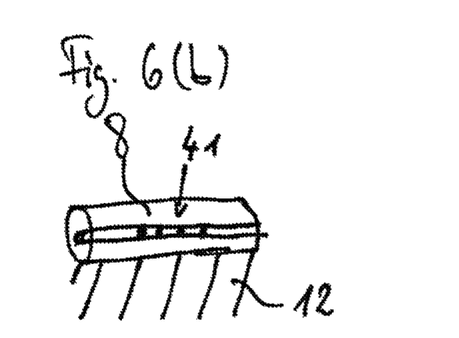

FIG. 6(b) schematically shows a fiber optic sensor of the blood pump 2, which comprises a fiber Bragg grating 41 for blood pressure measurement. The fiber Bragg grating 41 comprises optical interference filter inscribed into the optical fiber 8, which during the use thereof, in this example, adjoins the blood of the patient. Wavelengths that are within a filter bandwidth are reflected by the fiber Bragg grating 41. The reflected spectrum changes as a result of a blood pressure-induced change in length of the optical fiber 8, so that the evaluation unit 15 is able to infer the blood pressure from this spectrum.

Figure 7:
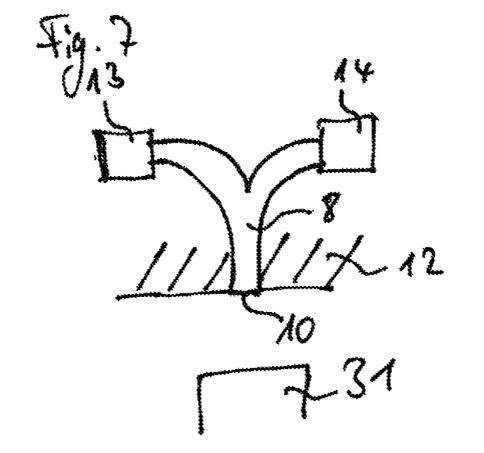
FIG. 7 shows a schematic view of a fiber optic sensor of the blood pump implemented as a sensor for determining a rotor position.

FIG. 7 shows a fiber optic sensor of the blood pump 2 for determining a position of the rotor 31. A fiber optic distance measurement can be used, which supplies reliable results, in provides in the case of light-reflecting surfaces. For example, the optical fiber, for this purpose, extends between the light source 13 or the light detector 14 and the flow channel 30 in such a way that the end face 10 faces the rotor 31.

The evaluation unit 15 is able to infer the distance or the position of the rotor 31 from an intensity of the light reflected by the rotor 31. In some embodiments, the light source 13 and the light detector 14 can also each be equipped with an optical fiber, wherein respective end faces of these optical fibers face the rotor 31.

Figure 8A:
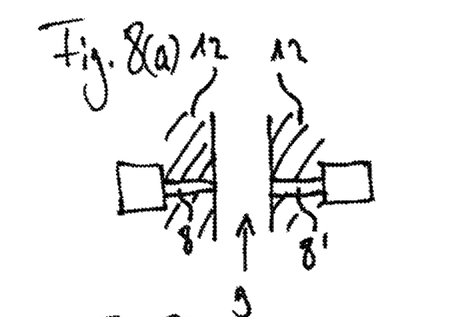
FIGS. 8(a) and (b) show schematic views of fiber optic sensors of the blood pump implemented as sensors for the detection of thrombi, a hematocrit value, a blood sugar level or a blood oxygen level.
Figure 8B:
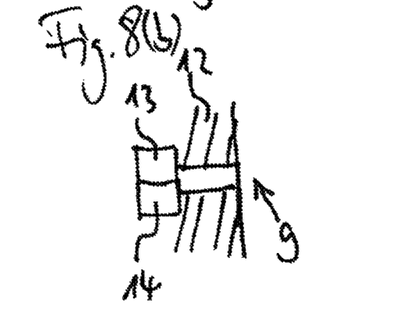

FIGS. 8(a) and (b) show schematic views of fiber optic sensors of the blood pump 2 implemented as sensors for the detection of thrombi, a hematocrit value, a blood sugar level or a blood oxygen level. During the hematocrit, blood sugar and oxygen measurement or thrombi detection, the transmitted or reflected light spectrum can be evaluated. A measured spectral distribution of the light can be compared to reference curves, for example in the evaluation unit 15. In this way, for example, the number of red blood cells, the oxygen saturation, the blood sugar level and/or the fibrin level can be measured, wherein the latter, in turn, allows conclusions as to the presence of thrombi to be drawn.

Features of the different embodiments only disclosed in the exemplary embodiments can be claimed combined with one another and individually.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A blood pump for supporting heart function, comprising:
    an implantable pump housing; and
    a fiber optic sensor including an optical fiber, the optical fiber being at least partially accommodated in a housing part of the pump housing;
    wherein the optical fiber is embedded into the housing part and contacts the housing part along at least a portion of the length of the optical fiber the contact providing a plastic-free seal between the optical fiber and the housing part and extending around a circumference of the optical fiber.

2. The blood pump of claim 1, wherein the optical fiber is welded into the housing part.

3. The blood pump of claim 2, wherein the optical fiber is welded into the housing part by way of ultrasonic welding.

4. The blood pump of claim 1, wherein the optical fiber comprises a plastic-free light-guiding core.

5. The blood pump of claim 4, wherein the light-guiding core comprises glass.

6. The blood pump of claim 1, wherein a plastic-free light-guiding core of the optical fiber makes direct contact with the housing part.

7. The blood pump of claim 1, wherein the optical fiber is material-bonded to the housing part.

8. The blood pump of claim 1, wherein the optical fiber is at least partially embedded into the housing part such as to extend circumferentially.

9. The blood pump of claim 1, wherein the fiber optic sensor is a blood pressure sensor.

10. The blood pump of claim 1, wherein the fiber optic sensor is a sensor for thrombi detection.

11. The blood pump of claim 1, wherein an end face of a fiber end of the optical fiber accommodated in the housing part of the pump housing is not completely covered by the housing part.

12. The blood pump of claim 11, wherein the fiber end is embedded into the housing part in such a way that the fiber end and the housing part form a plastic-free seal.

13. The blood pump of claim 11, wherein the optical fiber, with the end face thereof, faces a flow channel for conveying blood which is at least partially delimited by an interior side of the housing part.

14. The blood pump of claim 13, wherein a conveying element arranged in the flow channel, the end face of the optical fiber being arranged at a section of the flow channel which is located upstream with respect to the conveying element.

15. The blood pump of claim 13, wherein a conveying element arranged in the flow channel, the fiber optical sensor being configured to detect a position of the conveying element.

16. The blood pump of claim 11, wherein the optical fiber, with the end face thereof, faces an outer side of the pump housing which is delimited by an exterior side of the housing part.

17. The blood pump of claim 1, wherein the housing part comprises titanium or is produced from titanium.

18. The blood pump of claim 1, wherein the housing part is an inlet cannula or a chamber half of the pump housing.

19. The blood pump of claim 1, wherein the fiber optic sensor comprises a second optical fiber, the optical fibers being arranged and designed in such a way that the fiber optic sensor is a fiber optic transmission sensor.

20. The blood pump of claim 1, wherein a second fiber optic sensor and the first fiber optic sensor are configured to measure a blood pressure in a flow channel for conveying blood which is delimited by an interior side of the housing part, and the second fiber optic sensor is configured to measure a blood pressure either in the flow channel or on an outer side of the pump housing.

21. A method for producing a pump housing of a blood pump, comprising:
    providing an optical fiber;
    providing a first metal piece;
    arranging the optical fiber on the first metal piece;
    at least partially covering the optical fiber with a second metal piece; and
    introducing ultrasonic energy into the first and/or the second metal piece, and thereby joining the first and second metal pieces, and enclosing the optical fiber in the metal pieces in such a way that the optical fiber is at least partially embedded circumferentially into a housing part that is formed of the first metal piece and the second metal piece, wherein the optical fiber is embedded into the housing part and contacts the housing part along at least a portion of the length of the optical fiber to form a plastic-free seal between the optical fiber and the housing part and extending around a circumference of the optical fiber.

* * * * *